US006207404B1

United States Patent
Miller et al.

(10) Patent No.: US 6,207,404 B1
(45) Date of Patent: Mar. 27, 2001

(54) COUMARIN-BASED CYP3A FLUORESCENT ASSAY REAGENTS

(75) Inventors: Vaughn P. Miller, Arlington; Charles L. Crespi, Marblehead, both of MA (US)

(73) Assignee: Gentest Corporation, Woburn, MA (US)

( * ) Notice: Subject to any disclaimer, the term of this patent is extended or adjusted under 35 U.S.C. 154(b) by 0 days.

(21) Appl. No.: 09/410,212

(22) Filed: Sep. 30, 1999

(51) Int. Cl.[7] ............................ C12Q 1/26; C12Q 1/00; C07D 311/02
(52) U.S. Cl. ............................ 435/25; 435/4; 435/968; 549/283; 514/457
(58) Field of Search .................. 435/25, 4, 968; 549/283; 514/457

(56) References Cited

U.S. PATENT DOCUMENTS

| | | | |
|---|---|---|---|
| 3,515,721 | 6/1970 | Ritter et al. | 260/247.2 |
| 5,100,914 | 3/1992 | Rendenbach-Mueller et al. | 514/457 |
| 5,247,099 | 9/1993 | Celebuski | 549/289 |
| 5,830,912 | 11/1998 | Gee et al. | 514/457 |
| 5,851,785 | 12/1998 | Aoyama et al. | 435/28 |

FOREIGN PATENT DOCUMENTS

| | | | |
|---|---|---|---|
| 275270 B2 | 2/1992 | (CS) | C07D/309/38 |
| 1246754 | 8/1967 | (DE) . | |
| 1451667 | 7/1966 | (FR) . | |
| 2008109 | 5/1979 | (GB) . | |
| 2211500 | 7/1989 | (GB) . | |
| WO/92/22545 | 12/1992 | (WO) . | |
| WO/93/15219 | 8/1993 | (WO) . | |
| WO 99/58710 | 11/1999 | (WO) . | |
| 2000004008 | * 1/2000 | (WO) . | |
| WO 00/22159 | 4/2000 | (WO) . | |

OTHER PUBLICATIONS

6001 Chemical Abstracts, vol. 103, No. 5, 1985, Sailaja, G. et al., Synthesis of 7–Ethoxy–3– Substituted– Aminomethyl–4–Methylcoumarins, p. 498; XP002121159 & Indian J. Chem., Sect. B, vol. 24, No. B2, 1985, pp. 206–207, India.

Kishore K. Khan et al., "Structure–Function Analysis of Human Cytochrome P450 3A4 Using 7–Alkoxycoumarins as Active–Site Probes," *Archives of Biochemistry and Biophysics*, vol. 373, No. 2 (2000) pp. 335–345. (No Date).

* cited by examiner

*Primary Examiner*—Louise N. Leary
(74) *Attorney, Agent, or Firm*—Wolf, Greenfield & Sacks, P.C.

(57) ABSTRACT

Novel fluorescent substrates of human cytochrome P450 enzymes are provided. Also provided are methods for their manufacture and use. These substrates are useful in assessing cytochrome P450 enzyme activity and in selecting compounds which inhibit cytochrome P450 enzyme activity and, in particular, for identifying potential adverse drug interactions which are mediated by inhibition of cytochrome P450 enzyme activity. The compounds are particularly useful for assessing cytochrome P450 CYP3A enzyme activity.

30 Claims, 1 Drawing Sheet

COUMARIN-BASED CYP3A FLUORESCENT ASSAY REAGENTS

FIELD OF THE INVENTION

This invention relates to the field of drug and xenobiotic metabolism. The invention includes novel cytochrome P450 fluorescent probe substrates, particularly novel P450 CYP3A fluorescent probe substrates, methods for their preparation and their use as assay reagents.

BACKGROUND OF THE INVENTION

Cytochromes P450 (CYP) are the principal enzymes for the oxidative metabolism of many drugs, procarcinogens, promutagens, and environmental pollutants. Cytochrome P450 is a heme-containing, membrane-bound, multienzyme system that is present in many tissues in vivo but is present at the highest level in liver. In human liver, it is estimated that there are 15–20 different xenobiotic-metabolizing cytochrome P450 forms. A standard nomenclature based on relatedness of amino acid sequences has been developed. Certain P450 forms (such as CYP3A4 and CYP2C19) are known to be polymorphic in humans and some (such as CYP1A2 and CYP3A4) are regulated in response to environmental chemicals. Competition for metabolism by a particular cytochrome P450 form is a principal mechanism of some clinically significant drug-drug interactions.

Identification of the enzymes responsible for metabolism is becoming an important aspect of drug development. Such identifications consider both the metabolism of the new drug as well as inhibition by the new drug. The identification of enzymes involved in metabolism of the new drug allows prediction, based on knowledge of the ability of coadministered drugs to inhibit the same enzymes, of which coadministered drugs may inhibit the metabolism of the new drug. This information can also be used to predict individual variability based on known metabolic polymorphisms. The identification of the enzymes most sensitive to inhibition by the new drug allows prediction, based on knowledge of which coadministered drugs are metabolized by the same enzyme, of which coadministered drug's metabolism may be inhibited by the new drug. Obtaining information for a series of drug candidates early in the drug discovery process can assist in the choice of the best drug candidate for further development.

CYP3A4 is the most abundant cytochrome P450 in the human liver and intestine. CYP3A4 is responsible for the metabolism of many important drugs, for example: opioid analgesics, corticosteroids, immunosuppressants, and anti-arrhythmics (Rendic, S. and F. J. Di Carlo (1997) Drug Metab Rev. 29, p.413–580). Inhibition of this enzyme by dietary compounds (for example, grapefruit juice) or drugs has been responsible for several clinical drug-drug interactions. The importance of this P450 in drug metabolism makes the screening for metabolism and inhibition of this enzyme important in drug development.

Assays for CYP3A have focused on the metabolism of drug molecules or drug candidates. Substrates such as testosterone or midazolam are effective in assessing CYP3A activity and inhibition, but are not amenable to high throughput screening assay technology (both require time consuming separation of CYP3A reaction products using HPLC). Also, neither of these substrates have the necessary fluorescent properties that make the substrate useful for in situ fluorescent plate analysis.

We have previously reported the use of the commercially available compound 7-benzyloxyresorufin (BzRes) as a fluorescent substrate for assessing CYP3A4 activity in a high throughput mode (See Crespi et al. Anal Biochem. 248, 188–190, (1997). However, the low enzymatic turnover and poor specificity of this substrate make it of limited utility.

The O-dealkylation of 7-alkoxycoumarins has been reported as a fluorometric assay for determining the metabolic differences between cytochrome P450 isoforms using microsomes from several rat tissues (Kobayashi, Y., Fang, X, Szklarz, G. D., and J. R. Halpert, (1998) Biochem. 37, pp6679–6688). The O-dealkylation of 7-pentoxy-, 7-hexoxy-, and 7-benzyloxycoumarin have been studied in rat liver microsomes (Mayer, R. T., Netter, K. J., Heubel, F., Hanemann, B, Buchheister, A., Mayer, G. K. and M. D. Burke, (1990) Biochem. Pharmacol. 40, pp1645–1655). 7-Ethoxy-4-trifluoromethylcoumarin is O-dealkylated by human CYP2B6 and other human P450s (Code et al., (1997) Drug Metab. Dispo. 25, pp985–993; Morse, M. A., and J. Lu (1998) J. Chrom. B, 708, pp290–293.). The first coumarin analog whose O-dealkylation is specific for a single human P450 was recently developed by us (U.S. Ser. No. 60/092, 995, entitled Novel CYP2D Fluorescent Assay Reagents).

SUMMARY OF THE INVENTION

The present invention relates to novel fluorescent substrates of the human cytochrome P450 enzymes, particularly CYP3A4. These substrates are useful in assessing CYP3A4 enzyme activity and in selecting compounds which inhibit CYP3A4 enzyme activity. Accordingly, the compounds and methods of the invention are useful for identifying potential adverse drug interactions mediated by inhibition of CYP3A4 enzyme activity.

The compounds of the invention are substrates that are specific for CYP3A and are characterized in having properties which permit the sensitive quantitation of CYP3A activity using in situ fluorescence analysis. To satisfy these requirements, the compounds of the invention include: 1) a 7-hydroxycoumarin core for easy fluorescence detection, 2) an electron-withdrawing group on the coumarin core, and 3) an 0-alkyl group which can be easily O-dealkylated by the enzyme.

According to one aspect of the invention, compounds of Formula I are provided:

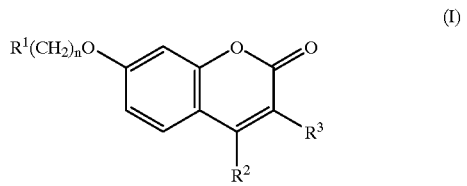

(I)

(a) wherein R1 is an aryl containing an aryl ring carbon and/or an aryl ring nitrogen and the $(CH_2)n$ is coupled via a covalent bond to the aryl ring carbon or the aryl ring nitrogen;

(b) wherein n is 0, 1, 2, or 3;

(c) wherein R2 is selected from the group consisting of an hydrido, CN, $CH_3$, sulfomethyl, and a haloalkyl containing from 1 to 18 carbons;

(d) wherein R3 is selected from the group consisting of an hydrido, CN, and an aryl containing an aryl ring carbon and/or an aryl ring nitrogen, provided that R2 and R3 are not both hydrido, and wherein the aryl is coupled directly to the coumarin ring via a covalent bond between the coumarin ring carbon and the aryl ring carbon or the aryl ring nitrogen;

(e) wherein when R1 is phenyl and n is 1, R2 is not an hydrido when R3 is phenyl and R3 is not an hydrido when R2 is CH$_3$; and (f) wherein the compound is a cytochrome P450 substrate.

Preferably, R1 is a phenyl and n is 1 or R1 is a naphthyl and n is 1.

In certain preferred embodiments, the R1 aryl is substituted with an electron donating group, (e.g., at the para position of a phenyl group). Exemplary electron donating groups include any of the following: an o-methoxy, an hydroxy, a primary amine (NH$_2$), a secondary amine (NR4R5, wherein R4 and R5 are independently selected from an alkyl containing from 1 to 5 carbon atoms); and a tertiary amine (NR4R5R6, wherein R4, R5, and R6 are independently selected from an alkyl containing from 1 to 5 carbon atoms).

In these and other embodiments, R2 preferably is selected from the group consisting of an hydrido, CN, CH$_3$, sulfomethyl, and a haloalkyl containing from 1 to 18 carbons. The most preferred R2 is an alkyl which is substituted to contain an electron-withdrawing group, e.g., a perfluoroalkyl having 1–18 carbons (such as CF$_3$) or CN. These substituted alkyl groups impart different fluorescent properties to the compounds of Formula I. Most notably, these electron-withdrawing groups increase the wavelengths for fluorescence excitation and emission. Thus, by altering the identity of the R2 group, one can predictably change the excitation and emission wavelengths of the fluorescent product which results from the action of a cytochrome P450 enzyme (e.g., CYP3A) on a compound of Formula I.

In these and other embodiments, R3 preferably is a hydrido, CN or an aryl selected from the group consisting of a phenyl, a benzoxazolyl, and a benzothiazolyl. Optionally, the R3 aryl is substituted with a halide (e.g., a chloro, a fluoro, a bromo, and an iodo) that may be the same or different from a halide contained in an R2 haloalkyl. These substituted aryls impart different fluorescent properties to the compounds of Formula I. Thus, by altering the identity of the R3 group, one can predictably change the excitation and emission wavelengths of the fluorescent product which results from the action of a cytochrome P450 enzyme (e.g., CYP3A) on a compound of Formula I.

Although various preferred embodiments are identified herein, it is to be understood that any combination of R groups can be used that is consistent with the compound as defined by formula I above. Thus, each of the substituent R1, R2, R3, R4, R5, and R6, is independently selected from the recited groups above. Preferably, the compounds of the invention are cytochrome P450 CYP3A substrates.

The most preferred embodiments of the invention include the following specific compounds:

(1) Name: 7-benzyloxy-4-trifluoromethylcoumarin (BFC, C$_{17}$H$_{11}$F$_3$O$_3$) [the compound of Formula I, wherein R3 is an hydrido, wherein R1 is phenyl, wherein n is 1, and wherein R2 is CF$_3$.]

(2) Name: 7-benzyloxy-3-cyanocoumarin [the compound of Formula I, wherein R2 is an hydrido, wherein R1 is phenyl, wherein n is 1, and wherein R3 is CN.]

(3) Name: 7-benzyloxy-3-cyano-4-methylcoumarin [the compound of Formula I, wherein R1 is phenyl, wherein n is 1, wherein R2 is CH3, and wherein R3 is CN.]

(4) Name: 7-(4-methoxy-benzyloxy)-4-trifluoromethylcoumarin [the compound of Formula I, wherein R3 is an hydrido, wherein R1 is p-methoxyphenyl, wherein n is 1, and wherein R2 is CF$_3$.]

(5) Name: 7-benzyloxy-3-(2-benzoxazolyl)coumarin [the compound of Formula I, wherein R2 is an hydrido, wherein R1 is phenyl, wherein n is 1, and wherein R3 is a 2-benzoxazolyl.]

(6) Name: 7-benzyloxy-3-(2-benzothiazolyl)coumarin [the compound of Formula I, wherein R2 is an hydrido, wherein R1 is phenyl, wherein n is 1, and wherein R3 is a 2-benzothiazolyl.]

(7) Name: 7-benzyloxy-3-(5-chloro-2-benzoxazolyl) coumarin [the compound of Formula I, wherein R2 is an hydrido, wherein R1 is phenyl, wherein n is 1, and wherein R3 is 5-chloro-2-benzoxazolyl.]

(8) Name: 7-(naphthalen-2-yloxy)-4-trifluoromethylcoumarin [the compound of Formula I, wherein R3 is an hydrido, wherein R1 is naphthyl, wherein n is 1, and wherein R2 is CF$_3$.

According to yet another aspect of the invention, a composition comprising a compound of Formula I is provided. The compound is present in the composition at a concentration greater than at least 50% by weight. The most preferred compositions contain a concentration of the compound of Formula I that is at least 80%, more preferably at least 90%, and most preferably at least 95% by weight. The preferred compositions are substantially free of detectable reaction product, i.e., the compositions of the invention do not contain levels of a cytochrome P450 (e.g., CYP3A)-catalyzed conversion product of a compound of Formula II.

The compounds of the invention may be contained in vials that are components of a kit for assaying a cytochrome P450 enzyme, such as a CYP3A enzyme activity.

The vials may contain preselected amounts of the compositions to facilitate dissolution of the contents to achieve a preselected concentration of the compound for performing a CYP3A enzyme assay. Accordingly, in certain embodiments of the invention, the compositions contain the appropriate buffers for performing an enzyme reaction in which the compound of Formula I serves as the substrate to form a fluorescent product.

Throughout this application, reference is made to determining CYP3A enzyme activity. It is to be understood that the reference to this particular cytochrome P450 enzyme is illustrative only and is not intended to limit the scope of the claimed compounds and methods to use in connection with detecting any one particular cytochrome P450 enzyme.

According to yet another aspect of the invention, a method for assaying a cytochrome P450 (e.g., CYP3A) enzyme activity is provided. The method involves contacting a CYP3A enzyme with a compound of Formula I. The assay may be performed in vivo or in vitro. For example, the compounds of the invention (e.g., the compounds of Formula I) can be administered to an animal model for, e.g., locating and, optionally, quantifying, CYP3A enzyme activity (e.g., by observing reaction products in biological fluid or tissue samples of the animal). More preferably, the method for assaying CYP3A enzyme activity is used to detect activity of a CYP3A that may be contained in biological fluid sample or solid sample (e.g., a tissue sample from liver, brain or intestine) or that may be expressed in a cell-containing or cell-free system (e.g., a microsome containing cDNA-expressed CYP3A). In this manner, conditions associated with deficiencies or over expression of CYP3A enzyme activity can be detected. Thus, the CYP3A enzyme may be contained in a sample that is a liver sample such as a crude homogenate, partially purified, or purified liver enzyme obtained from a biopsy, a cDNA-expressed CYP3A, in hepatocytes, or in microsomes.

The cytochrome P450 enzyme catalyzes the conversion of the compound to a fluorescent product. In the most preferred embodiments, the product produced by the process of allowing a CYP3A enzyme to react with a compound of Formula I is Compound II (HFC, $C_{10}H_5F_3O_3$), Name: 7-hydroxy-4-trifluoromethylcoumarin.

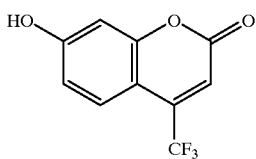

(Compound II)

More generally, fluorescent products of the cytochrome P450 enzyme reaction are compounds of Formula II, i.e., the compounds of Formula II are produced as a reaction product of the CYP3A-catalyzed reaction of a substrate that is a compound of Formula I. In general, these compounds have structures that differ from those of the compounds of Formula I in having a hydroxy group at position 7 of the coumarin ring. Formula II is presented below; the substituent groups are as defined above in reference to Formula I:

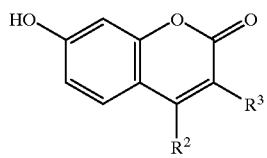

(II)

According to yet another aspect of the invention, a screening method for identifying agents which inhibit a cytochrome P450 (e.g., CYP3A) enzyme activity is provided. The method involves contacting a CYP3A enzyme with a compound of Formula I in the presence of a putative CYP3A enzyme inhibitor and under conditions whereby the cytochrome P450 enzyme catalyzes the conversion of the compound to a fluorescent product, and selecting an agent which inhibits cytochrome P450 enzyme activity as a cytochrome P450 enzyme inhibitor. In the preferred embodiments, the screening method is a high throughput screening assay. For example, the compound can be contacted with the putative cytochrome P450 enzyme inhibitor in a multiwell plate well and the fluorescence automatically detected and recorded. Alternatively, the compounds of Formula I can be distributed into one or more wells or vials, which are then lyophilized or otherwise dried to provide a product having an enhanced shelf life. If the product is provided for use in a kit for measuring CYP3A enzyme activity, the kit can further contain instructions for redissolving the compound of Formula I and, optionally, an appropriate buffer (e.g., enzyme reaction buffer) for effecting the dissolution.

According to another aspect of the invention, a method for visualizing a cytochrome P450 (e.g., CYP3A) enzyme is provided. The method involves contacting a CYP3A enzyme-containing sample with a compound of Formula I and subjecting the CYP3A enzyme and the compound to conditions whereby the CYP3A enzyme catalyzes the conversion of the compound of Formula I to a fluorescent product. In the preferred embodiments, the method for visualizing a CYP3A enzyme is performed on a tissue section sample, e.g., the CYP3A enzyme-containing sample is a tissue section such as derived from a biopsy sample.

According to still another aspect of the invention, kits for detecting and/or measuring cytochrome P450 (e.g., CYP3A) enzyme activity are provided. The kits contain a compound of Formula I and instructions for using the kits to measure CYP3A enzyme activity. The preferred compounds of Formula I are compounds which have a high specificity of binding for the enzyme and for which the enzyme exhibits a high rate of substrate turnover. These parameters typically are reflected in the Km and Vmax values for the enzyme-catalyzed conversion of the substrate (i.e., compound of the invention) to a fluorescent product. In general, a higher relative affinity of the CYP3A enzyme for a first substrate compared to a second substrate is indicated by a lower Km value for the first substrate compared to the second substrate. A higher catalytic turnover for a first substrate compared to a second substrate is indicated by a higher Vmax for the first substrate. The preferred compounds of the invention have a Km of greater than about 50 nM with a Vmax greater than about 0.05 $min^{-1}$. In general, the compounds of the invention have a Km greater than 1 uM and a Vmax from about 0.05 to about 20 $min^{-1}$, with a preferred range for Km being greater than about 1 uM and a preferred range for Vmax being from about 0.2 to about 20 $min^{-1}$. In general, the compounds of the invention have a Km greater than 1 uM and a Vmax from about 0.05 to about 20 $min^{-1}$, with a preferred range for Km being greater than about 1 uM and a preferred range for Vmax being from about 0.2 to about 20 $min^{-1}$.

According to yet another aspect of the invention, certain embodiments of the fluorescent cytochrome P450 reaction products which employ the compounds of Formula I as a substrate are provided, i.e., the fluorescent products are produced as a reaction product of a cytochrome P450 (e.g., CYP3A)-catalyzed reaction of a substrate that is a compound of Formula I. In general, these compounds (the compounds of Formula II) have structures that differ from those of the compounds of Formula I in having a hydroxy group at position 7 of the coumarin ring.

These and other aspects of the invention as well as various advantages and utilities will be more apparent with reference to the detailed description of the preferred embodiments. All patents, patent publications and references identified in this document are incorporated in their entirety herein by reference.

BRIEF DESCRIPTION OF THE DRAWINGS

The Examples reference figures for illustrative purposes only. The figures are not essential for enablement of the invention as claimed.

DETAILED DESCRIPTION OF THE INVENTION

I. Definitions

Figure 1:
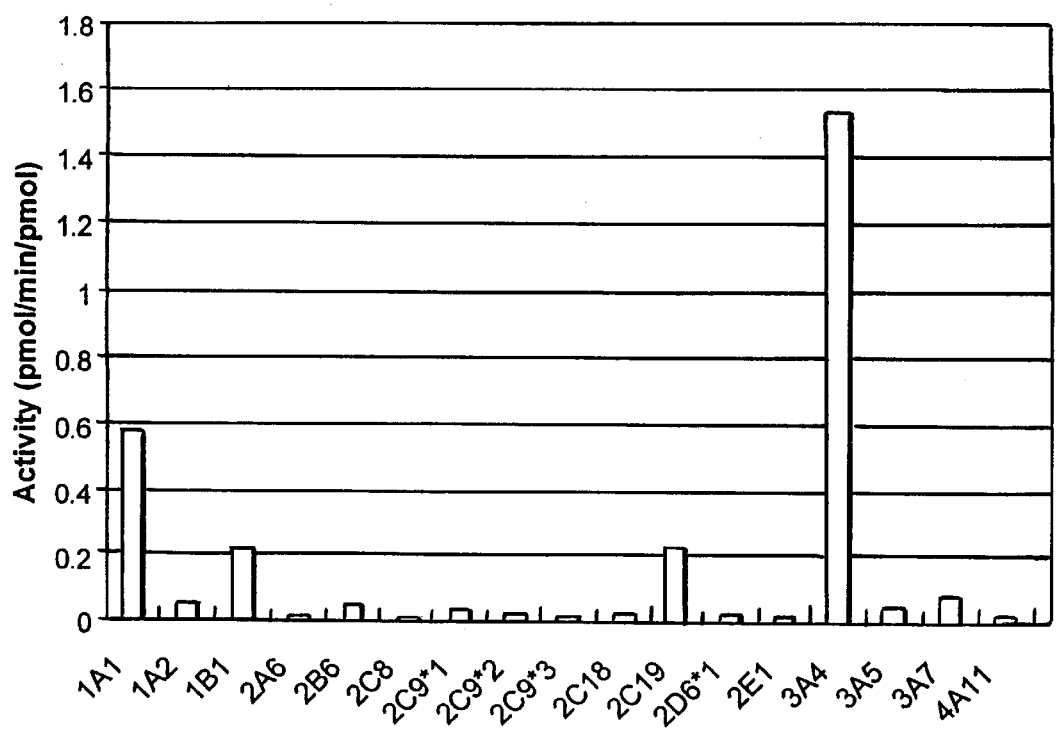
FIG. 1 illustrates the selectivity of Compound I dealkylation by a panel of human P450 enzymes.

Throughout this document CYP3A is used in reference to the enzyme which catalyzes the conversion of a compound of the invention to a fluorescent product. It is to be understood that any member of the cytochrome P450 family or, more particularly, the CYP3A family, can be used in any of the enzyme reactions discussed herein and that CYP3A4 represents a particularly preferred embodiment of the invention.

Molecular terms, when used in this application, have their common meaning unless otherwise specified. The term hydrido denotes a single hydrogen atom. The term amino denotes a nitrogen atom containing two substituents that can be the same or different. The amino group substituents are independently selected from the group consisting of hydrido, alkyl, cycloalkyl, and aryl groups.

Alkyl groups can be linear or branched, saturated or unsaturated, and have up to 10 carbon atoms. The preferred alkyl groups are saturated. More preferably, the alkyl groups are lower alkyl groups having from 1–5 carbon atoms, inclusive. Exemplary alkyl groups include methyl, ethyl, propyl, butyl, and pentyl. Additional exemplary alkyl groups include isopropyl and tert-butyl. One or more hydrogen atoms may also be replaced by a halo to form a haloalkyl. A preferred haloalkyl contains from 1 to 18 carbon atoms. More preferably, the haloalkyl is a perhaloalkyl, such as a perfluoroalkyl, with the most preferred fluoroalkyl being $CF_3$.

Aryl groups can contain from 0–4 hetero atoms selected from oxygen, nitrogen and sulfur in a single or fused carbocyclic or heterocyclic ring system, having from 5–15 ring members. One or more hydrogen atoms may also be replaced by a substituent group selected from an acyl, an amino, a carboalkoxy, a carboxy, a carboxyamido, a cyano, a halo, a hydroxy, a nitro, a thio, an alkyl, an aryl, a cycloalkyl, an alkoxy, an aryloxy, a sulfoxy, and a guanido group.

A preferred class of aryl groups are unsubstituted phenyl groups and phenyl groups in which one or more hydrogen have been replaced with an alkyl, alkoxy, aryloxy, or halo group. Exemplary aryl groups include phenyl, phenyl naphthyl, biphenyl, terphenyl, pyridinyl, and various other phenyl derivatives.

Cycloalkyl groups have, preferably, saturated or partially unsaturated ring systems, each containing zero to four hetero atoms selected from oxygen, nitrogen and sulfur in a single or fused carbocyclic or heterocyclic ring system having from three to fifteen ring members. One or more hydrogen atoms may also be replaced by a substituent group selected from acyl, amino, carboalkoxy, carboxy, carboxyamido, cyano, halo, hydroxy, nitro, oxo, thio, alkyl, aryl, cycloalkyl, alkoxy, aryloxy, and guanido groups or two substituents together may form a fused cycloalkyl ring. Examples of a cycloalkyl group include cyclopropyl, cyclobutyl, cyclohexyl, cycloheptyl, morpholinyl, piperidinyl, and pyrolidinyl. An alkoxy group denotes an oxygen atom substituted with an acyl, alkyl or cycloalkyl group. Examples include methoxy, tert-butoxy, benzyloxy, and cyclohexyloxy. An aryloxy groups denotes an oxygen atom substituted with an aryl group. Examples of aryloxy groups are phenoxy, 4-carbobenzyloxyphenoxy, 4-phenoxyphenoxy. Preferred aryloxy groups are phenoxy and substituted phenoxy groups. Sulfoxy groups comprise a hexavalent sulfur atom bound to two or three substituents selected from the group consisting of oxo, alkyl, aryl and cycloalkyl groups, wherein at least one of said substituents is oxo.

II. Description

The invention provides compounds of Formula I, methods for their manufacture and use. The compounds of Formula I are useful for assaying the activity of a cytochrome P450 enzyme, such as a CYP3A family member. The compounds are particularly useful for measuring the potential inhibition of CYP3A4, preferably in a high throughput screening assay. For example, the invention provides a method for assaying CYP3A which involves contacting a CYP3A enzyme with a compound of Formula I under the conditions in which the CYP3A enzyme interacts with the compound of Formula I and catalyzes dealkylation at the 7 position of the compound to form a 7-hydroxy coumarin product. Such conditions are known to those skilled in the art (see also, e.g., the Examples for conditions). This method can be performed using in vivo or in vitro sources of enzyme CYP3A. In a further aspect, the invention provides a method for assessing the potential CYP3A inhibition of a test chemical, preferably in a high throughput screening assay. Such conditions are known to those skilled in the art and are exemplified in the Examples.

The structures of the compounds of the invention, particularly the structures of Formula I, are provided in the Summary and in the Claims.

GENERAL SYNTHETIC PROCEDURES

General Procedure 1

A compound of Formula II or a commercially available reagent is converted to a compound of Formula I by treatment with reagent A and a base such as potassium carbonate in an appropriate solvent such as tetrahydrofuran, acetone, dimethyl sulfoxide, acetonitrile, or dimethylformamide at temperatures ranging from 0° C. to 75° C. A preferred compound for performing the synthesis reaction is Compound IIa (Registry No. 575-03-1, Name: 7-hydroxy-4-trifluoromethylcoumarin), available commercially (Aldrich Chem. Co., Milwaulkee, Wis.), to yield a preferred compound of Formula I, Compound I (BFC).

Reaction 1

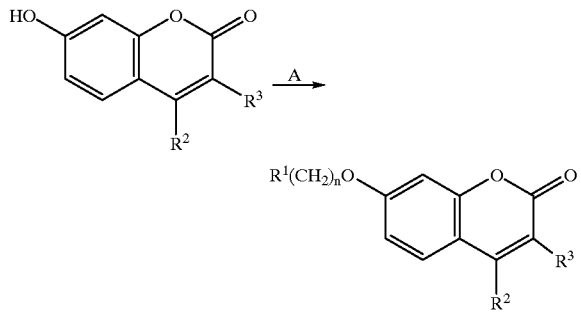

wherein each of R1, R2, and R3 are defined as above; wherein A is an alcohol alkylating reagent such as, benzyl-bromide.

EXAMPLES

The following examples are detailed descriptions of the methods of making and using the compounds of Formula I. These detailed preparations fall within the scope of, and serve to exemplify, the above described General Procedures which form part of the invention. These Examples are presented for illustrative purposes only and are not intended to limit the scope of the invention.

Example 1:

7-Benzyloxy-4-trifluoromethylcoumarin (Compound I)

A. Preparation of Compound I.

7-Hydroxy-4-trifluoromethylcoumarin (6.0 g, 26.06 mmol) was dissolved in acetonitrile (300 mL) then potassium carbonate (7.2 g, 52.17 mmol) and benzylbromide (3.1 mL, 26.06 mmol) were added. After stirring 24 h at room temperature, the solvent was evaporated under reduced pressure. The resulting white solid was taken up in methylene chloride (300 mL), washed with water (5×100 mL) and dried over anhydrous sodium sulfate. The solvent was evaporated under reduced pressure and the residue was chromatographed on silica gel using hexanes (100%) then hexanes/ethyl acetate (75/25) as eluents. A white solid, which was the title compound 7-benzyloxy-4-trifluoromethylcoumarin, was obtained (6.09 g, 78%). Melting point: 103.5–104.5C. $^1$H-NMR (CDCl$_3$): 7.67–7.60 (1H, m, ArH), 7.44–7.35 (5H, m, PhH), 7.05–6.97 (1H, m, ArH), 6.94–6.93 (1H, m, ArH), 6.62 (1H, s, ArH), 5.15 (2H, s, PhCH$_2$).

TABLE I

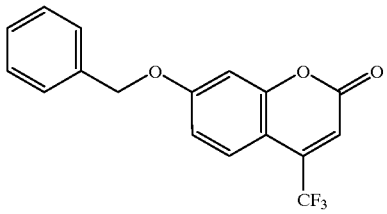

| # | Structure | General Procedure |
|---|-----------|-------------------|
| I | 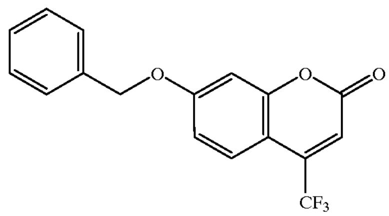          | 1                 |

Biological Evaluation.

The evaluation of compounds of Formula I for usefulness as CYP3A substrates includes: (1) Enzyme kinetics for the compounds of Formula I were performed using cDNA-expressed CYP3A; (2) The specificity of the compounds of Formula I as substrates for CYP3A were examined using a panel of cDNA-expressed human P450 enzymes; (3) The IC$_{50}$ values for known inhibitors of CYP3A4, measured in a high throughput screening assay, of compounds of Formula I, were correlated with those values from known substrates useful for this application; (4) The same inhibition screen as in (3) was evaluated using human liver microsomes as the enzyme source.

(1) Enzyme Kinetics with cDNA-expressed CYP3A4

The evaluation of compounds of Formula I were initially performed by measuring the kinetics of turnover using cDNA-expressed CYP3A4. In most instances, Vmax and Km values are important for the optimization of the assay conditions and for setting the parameters for inhibition experiments. Fluorometric assays for the turnover of compounds of Formula I by CYP3A4 were performed based on a modification of the method by Crespi et al. *Anal Biochem.* 248, 188–190, (1997), (described below). Comparisons of the enzyme kinetics (Table II) for compounds of Formula I and the substrate benzyloxyresorufin (BzRes) show that CYP3A4 has a lower affinity for compounds of Formula I (higher Km), but compounds of Formula I have a higher catalytic turnover (higher Vmax).

The foregoing results exemplify one of the primary advantages of the compounds of the invention compared to the prior art substrates in detecting and/or quantifying cytochrome P450 enzyme activities, particularly in reference to 3A4 enzyme activity determinations. The compounds of the invention exhibit a surprising and unexpected, statistically significant higher $V_{max}$ value (at least about 4 to 5-fold greater) compared to a reference prior art substrate (benzyloxyresorufin) (see Table II).

TABLE II

| Compound # | K$_m$ (uM) | V$_{max}$(min$^{-1}$) |
|------------|------------|------------------------|
| I          | >200 uM (exceeds solubility) | 1.5 at 40 uM |
| Benzyloxyresorufin (BzRes) | 38 | 0.3 |

Example Compound I. Assays were conducted in 96 well microtiter plates (Corning COSTAR, cat. no. 3915). The substrate, compound I, was prepared in acetonitrile. After cofactors addition, the plates were prewarmed to 37° C. Incubations were initiated by the addition of prewarmed buffer and enzyme. The enzymes were commercially available, baculovirus/insect cell expressed human CYP3A4 (SUPERSOMES®, GENTEST Corporation). The amount of enzyme added per well was 1 pmole. The final cofactor concentrations were 1.3 mM NADP, 3.3 mM glucose-6-phosphate, 3.3 mM MgCl$_2$ and 0.4 U/ml glucose-6-phosphate dehydrogenase. Final incubation volume was 0.2 ml. Incubations were carried out for 45 minutes and stopped by the addition of 0.075 ml of 80% acetonitrile, 20% 0.5 M Tris base. Fluorescence per well was measured using a BMG FLUOstar Model 403 plate scanner controlled with an IBM-compatible computer. The metabolite was measured using an excitation wavelength of 410 nm and emission wavelength of 538 nm. Data was exported and analyzed using an Excel spreadsheet. The activity was quantified by comparing to a standard curve of 7-hydroxy-4-trifluoromethyl coumarin.

(2) Selectivity in a Panel of cDNA-Expressed P450 Enzymes

The selectivity of various P450 isoforms for dealkylation of compound I was examined using a panel of commercially available human cDNA-expressed enzymes. A substrate that is selective for a single P450 isoform (substrate is catalytically turned over by a single P450 isoform) is a desirable trait in that its activity may be examined within a heterogeneous mixture of enzymes, for example, in human liver microsomes. The previously published high throughput screening substrate, benzyloxyresorufin (BzRes) is significantly metabolized by other human cytochromes P450 (Ono et al. (1996) Xenobiotica 26, 681–693). Comparison of the catalytic selectivity for compounds of Formula I is shown in FIG. I. Compound I is selective for CYP3A4. Compound I is particularly selective in human liver microsomes since CYP1A1 (the second best enzyme) is not found in these tissue preparations. Compound I is therefore a more useful substrate for probing CYP3A activity in a heterogeneous mixture than the previous substrate BzRes. These advantages permit the specific detection of low levels of a preselected cytochrome P450 enzyme (e.g., 3A4) contained in various types of samples, e.g., tissue samples, microsomes, and so forth.

Example Compound I. Assays were conducted as described in (1) above except: incubation time was 20 min.; enzymes were commercially available, baculovirus/insect cell expressed human P450s (SUPERSOMES®, GENTEST Corporation); and the amount of enzyme added per well was 10 pmole with the exception of 2.5 pmole for CYP3A enzymes.

(3) High Throughput CYP3A4 Inhibition Screen

The measurement of the CYP3A4 inhibition potential of compounds of Formula I was based on a modification of the published method by Crespi et al. *Anal Biochem.* 248, 188–190, (1997). This published study examined the IC$_{50}$ for the potent CYP3A4 inhibitor ketoconazole using BzRes as a substrate. Good agreement was seen with inhibition kinetics for ketoconazole and human liver microsomes. A series of CYP3A4 selective inhibitors was examined in this system, using BzRes, or compounds of Formula I as a substrate. IC$_{50}$ values were not always found to be highly correlated. This is consistent with the idiosyncrasies in the inhibition kinetics encountered with this enzyme [Korzekwa K R et al *Biochemistry* 37, 4137–4147, (1998)]. Additionally, in some cases, the test compound activated the enzyme. The higher turnover along with the greater quantum yield of the product (7-hydoxy-4-trifluoromethylcoumarin) relative to the product of benzyloxyresorufin (BzRes) has distinct advantages. Lower amounts of enzyme can be used to achieve the required signal in the inhibition assay. Thus, there is a lower potential for depleting the inhibitor through metabolism by CYP3A4. Inhibition experiments conducted with compound I as the substrate tend to yield lower $IC_{50}$ values. Therefore, the assay using compound I is more likely to properly detect problematic compounds before they are developed into human pharmaceuticals.

Example Compound I. Assays were conducted in 96 well microtiter plates. The substrates, compounds of Formula I, were prepared in acetonitrile. The substrate stock concentrations were twice the final concentration (final concentration chosen to be below the apparent $K_m$, for example 100 uM for compound I). The 12 wells in a row were used for one test. Wells 1 to 8 contained serial 1:3 dilutions of the inhibitors. Wells 9 and 10 contained no inhibitor and rows 11 and 12 were blanks for background fluorescence (stop solution added before the enzyme). After substrate and inhibitor addition, the plates were prewarmed to 37° C. Incubations were initiated by the addition of prewarmed enzyme and cofactors. The enzyme was commercially available, baculovirus/insect cell expressed human CYP3A4 (SUPERSOMES®, Cat. no. P202, GENTEST Corporation). The amount of enzyme added per well was 1 pmole. The final cofactor concentrations were 1.3 mM NADP, 3.3 mM glucose-6-phosphate, 3.3 mM $MgCl_2$ and 0.4 U/ml glucose-6-phosphate dehydrogenase. The final concentration of protein was 0.25 mg/mL which included insect cell control protein (Cat. no. P201, GENTEST Corporation) in addition to CYP3A4. Final incubation volume was 0.2 ml. Incubations were carried out for 20 minutes and stopped by the addition of 0.075 ml of 80% acetonitrile, 20% 0.5 M Tris base. Fluorescence per well was measured using a BMG FLUOstar Model 403 plate scanner controlled with an IBM-compatible computer. The metabolite was measured using an excitation wavelength of 410 nm and emission wavelength of 538 nm. Data was exported and analyzed using an Excel spreadsheet. The $IC_{50}$ values were calculated by linear interpolation.

TABLE III

CYP3A4 HTS Substrates: $IC_{50}$ Values (uM)

| Inhibitor | Substrate BzRes | I |
|---|---|---|
| Itraconazole | 0.265 | 0.054 |
| Ketoconazole | 0.034 | 0.005 |
| (+/−)Miconazole | 0.148 | 0.035 |
| Erythromycin | 1.697 | 4.074 |
| Cisapride | 0.158 | 0.035 |
| Posicor | 0.023 | 0.007 |
| Midazolam | 68.383 | 0.643 |
| Clotrimazole | 0.013 | 0.003 |
| Nifedipine | 10.807 | 7.190 |
| Cyclosporin | 3.280 | 3.636 |

(4) CYP3A4 Inhibition Screen Using Human Liver Microsomes

Human liver microsomes are a common source of human cytochromes P450 for in vitro drug metabolism studies. Because these tissue derived microsomes contain a mixture of P450 enzymes at relatively low concentrations, the study of a single enzyme in this mixture requires a probe substrate with high catalytic turnover and selectivity. The data described in 1 and 2 above using cDNA-expressed CYP3A4 suggested Compound I may be used with human liver microsomes.

Figure 2:
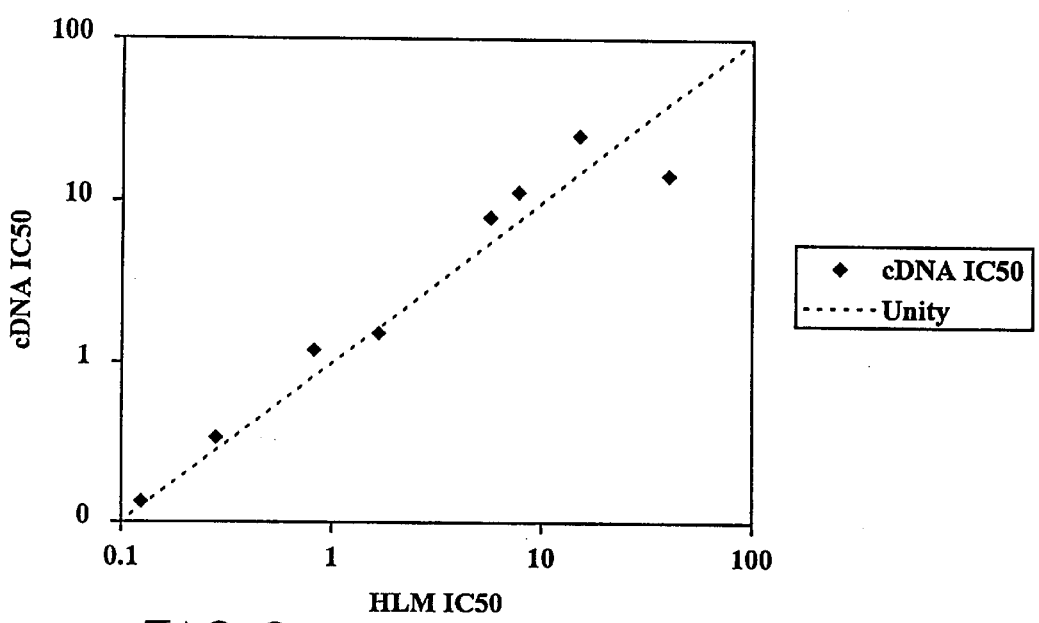
FIG. 2 illustrates HLM vs. cDNA IC50 comparison.

The measurement of the CYP3A4 inhibition potential of compounds of Formula I using cDNA-expressed CYP3A4 and human liver microsomes was performed using the method described in 3 above. A strong correlation in $IC_{50}$ values (FIG. 2) for a series of selective CYP3A4 inhibitors (Table IV) was seen between the two sources of human CYP3A4. Therefore Compound I can be used as a fluorescent probe substrate to study the activity and inhibition of CYP3A4 using human liver microsomes as well as cDNA-expressed CYP3A enzyme.

Example Compound I. Assays were conducted in the same manner as described in (3) above with the following exceptions. The amount of cDNA-expressed CYP3A4 enzyme added per well was 5 pmole. The amount of human liver microsomes (donor HG48, GENTEST Corporation) added per well was 0.25 mg of protein. The inhibitors studied are in Table IV.

TABLE IV

| Inhibitor |
|---|
| Itraconazole |
| Ketoconazole |
| (+/−)Miconazole |
| Erythromycin |
| Cisapride |
| Terfenadine |
| Midazolam |
| Nifedipine |

The preceding is merely a detailed description of certain preferred embodiments. It therefore should be apparent to those skilled in the art that various modifications and equivalents can be made without departing from the spirit or scope of the invention.

What is claimed is:

1. A compound of the Formula I:

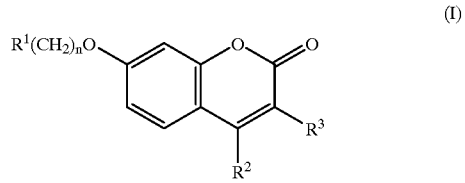

(I)

(a) wherein R1 is an aryl containing an aryl ring carbon and/or an aryl ring nitrogen and the $(CH_2)n$ is coupled via a covalent bond to the aryl ring carbon or the aryl ring nitrogen;

(b) wherein n is 0, 1, 2, or 3;

(c) wherein R2 is selected from the group consisting of an hydrido, CN, $CH_3$, sulfomethyl, and a haloalkyl having 1–18 carbons;

(d) wherein R3 is selected from the group consisting of an hydrido, CN, and an aryl containing an aryl ring carbon and/or an aryl ring nitrogen, provided that R2 and R3 are not both hydrido, and wherein the aryl group is coupled directly to the coumarin ring via a covalent bond between the coumarin ring carbon and the aryl ring carbon or the aryl ring nitrogen;

(e) wherein when R1 is phenyl and n is 1, R2 is not an hydrido when R3 is phenyl and R3 is not an hydrido when R2 is $CH_3$;

(f) wherein the compound is a cytochrome P450 substrate.

2. The compound of claim 1, wherein R1 is a phenyl and n is 1.

3. The compound of claim 1, wherein R1 is a naphthyl and n is 1.

4. The compound of claim 1, wherein the aryl ring is substituted with an electron donating group (e.g., a para-substituted phenyl).

5. The compound of claim 4, wherein the electron donating group is selected from the group consisting of an o-methoxy, an hydroxy, a primary amine ($NH_2$), a secondary amine (NR4R5, wherein R4 and R5 are independently selected from an alkyl containing from 1 to 5 carbon atoms); and a tertiary amine (NR4R5R6, wherein R4, R5, and R6 are independently selected from an alkyl containing from 1 to 5 carbon atoms).

6. The compound of claim 1, wherein R4 is a hydrido.

7. The compound of claim 6, wherein R2 is CN.

8. The compound of claim 6, wherein R2 is $CH_3$.

9. The compound of claim 6, wherein R2 is sulfomethyl.

10. The compound of claim 6, wherein R2 is a haloalkyl having from 1 to 18 carbon atoms.

11. The compound of claim 1, wherein R3 is an hydrido.

12. The compound of claim 1, wherein R3 is CN.

13. The compound of claim 1, wherein R3 is an aryl.

14. The compound of claim 1, wherein R3 is an aryl selected from the group consisting of a phenyl, a benzoxazolyl, and a benzothiazolyl.

15. The compound of claim 1, wherein R3 is an aryl substituted with a halide that may be the same or different from the halide contained in an R2 haloalkyl.

16. The compound of claim 1, wherein the halide contained in an R2 haloalkyl and the halide contained in an R3 aryl substituted with a halide are independently selected from the group consisting of a chloro, a fluoro, a bromo, and an iodo.

17. The compound of claim 1, wherein the compound is a cytochrome P450 CYP3A substrate.

18. The compound of claim 1, wherein R3 is an hydrido, wherein R1 is phenyl, wherein n is 1, and wherein R2 is $CF_3$.

19. The compound of claim 1, wherein R2 is an hydrido, wherein R1 is phenyl, wherein n is 1, and wherein R3 is CN.

20. The compound of claim 1, wherein R1 is phenyl, wherein n is 1, wherein R2 is CH3, and wherein R3 is CN.

21. The compound of claim 1, wherein R3 is an hydrido, wherein R1 is p-methoxyphenyl, wherein n is 1, and wherein R2 is $CF_3$.

22. The compound of claim 1, wherein R1 is phenyl, wherein n is 1, and wherein R3 is a 2-benzoxazolyl.

23. The compound of claim 1, wherein R2 is an hydrido, wherein R1 is phenyl, wherein n is 1, and wherein R3 is a 2-benzothiazolyl.

24. The compound of claim 1, wherein R2 is an hydrido, wherein R1 is phenyl, wherein n is 1, and wherein R3 is 5-chloro-2-benzoxazolyl.

25. The compound of claim 1, wherein R3 is an hydrido, wherein R1 is naphthyl, wherein n is 1, and wherein R2 is $CF_3$.

26. A composition comprising a compound of claim 1, wherein the compound is present in the composition at a concentration greater than at least 50% by weight.

27. The composition of claim 26, wherein the compound is present in the composition at a concentration greater than at least 95% by weight.

28. A method for assaying cytochrome P450 enzyme activity comprising:
   contacting a cytochrome P450 enzyme with a compound of formula I as defined by claim 1;
   under conditions whereby the cytochrome P450 enzyme catalyzes the conversion of the compound to a fluorescent product.

29. A screening method for selecting agents which inhibit cytochrome P450 enzyme activity comprising:
   contacting a cytochrome P450 enzyme with a compound of formula I as defined by claim 1,
   in the presence of a putative cytochrome P450 enzyme inhibitor, and under conditions whereby the cytochrome P450 enzyme catalyzes the conversion of the compound to a fluorescent product; and
   selecting an agent which inhibits cytochrome P450 enzyme activity as a cytochrome P450 enzyme inhibitor.

30. A method for visualizing a cytochrome P450 enzyme comprising:
   contacting a cytochrome P450 enzyme-containing sample with a compound of formula I as defined by claim 1,
   and subjecting the cytochrome P450 enzyme and the compound to conditions whereby the cytochrome P450 enzyme catalyzes the conversion of the compound to a fluorescent product.

* * * * *